(12) United States Patent
Speth et al.

(10) Patent No.: US 10,517,971 B2
(45) Date of Patent: Dec. 31, 2019

(54) SYSTEMS AND METHODS FOR STERILIZING SEALED RADIONUCLIDE GENERATOR COLUMN ASSEMBLIES

(71) Applicant: Curium US LLC, St. Louis, MO (US)

(72) Inventors: Andrew D. Speth, St. Charles, MO (US); Mark A. Spinelli, Sr., O'Fallon, MO (US); Gregory P. Wehmer, Florissant, MO (US); Bryan S. Petrofsky, St. Louis, MO (US)

(73) Assignee: Curium US LLC, St. Louis, MO (US)

( * ) Notice: Subject to any disclaimer, the term of this patent is extended or adjusted under 35 U.S.C. 154(b) by 280 days.

(21) Appl. No.: 15/410,952

(22) Filed: Jan. 20, 2017

(65) Prior Publication Data

US 2017/0319724 A1    Nov. 9, 2017

Related U.S. Application Data

(60) Provisional application No. 62/331,616, filed on May 4, 2016.

(51) Int. Cl.
| | |
|---|---|
| *A61L 2/07* | (2006.01) |
| *G21G 4/08* | (2006.01) |
| *A61L 2/24* | (2006.01) |
| *G21G 1/00* | (2006.01) |

(52) U.S. Cl.
CPC .......... *A61L 2/07* (2013.01); *A61L 2/24* (2013.01); *G21G 4/08* (2013.01); *A61L 2202/11* (2013.01); *A61L 2202/14* (2013.01); *A61L 2202/15* (2013.01); *G21G 1/0005* (2013.01)

(58) Field of Classification Search
CPC .................................. A61L 2/07; G21G 4/08
See application file for complete search history.

(56) References Cited

U.S. PATENT DOCUMENTS

| | | |
|---|---|---|
| 3,369,121 A | 2/1968 | Bruno et al. |
| 3,576,998 A | 5/1971 | Deutsch et al. |
| 3,709,365 A | 1/1973 | Czaplinski et al. |
| 3,774,035 A | 11/1973 | Litt |
| 3,920,995 A | 11/1975 | Czaplinski et al. |
| 3,970,583 A | 7/1976 | Panek-Finda |
| 5,109,160 A | 4/1992 | Evers |

(Continued)

FOREIGN PATENT DOCUMENTS

RU    2546731 C1    4/2015

OTHER PUBLICATIONS

International Search Report and Written Opinion of the International Searching Authority regarding PCT/US2017/014277 dated Oct. 17, 2017; pp. 1-12.

*Primary Examiner* — Kevin Joyner
(74) *Attorney, Agent, or Firm* — Armstrong Teasdale LLP (57) ABSTRACT

Systems and methods for sterilizing a column assembly including a column having an interior containing a retaining media and a parent radionuclide retained by the retaining media, an inlet port in fluid communication with the interior of the column, and an outlet port in fluid communication with the interior of the column. The method includes sealing at least one of the inlet port and the outlet port to form a sealed column assembly such that fluid communication with the column interior though both the inlet port and the outlet port is prevented, and sterilizing the sealed column assembly to form a terminally-sterilized column assembly.

15 Claims, 6 Drawing Sheets

(56) References Cited

U.S. PATENT DOCUMENTS

| | | | |
|---|---|---|---|
| 6,157,036 | A | 12/2000 | Whiting et al. |
| 7,091,494 | B2 | 8/2006 | Weisner et al. |
| 8,058,632 | B2 | 11/2011 | Balestracci et al. |
| 8,569,713 | B2 | 10/2013 | Evers |
| 8,822,950 | B2 | 9/2014 | Evers |
| 8,866,104 | B2 | 10/2014 | Mayfield et al. |
| 2005/0116186 | A1 | 6/2005 | Weisner et al. |
| 2005/0253085 | A1 | 11/2005 | Weisner et al. |
| 2009/0129989 | A1 | 5/2009 | Balestracci et al. |
| 2011/0292195 | A1 | 12/2011 | Dahmen |
| 2012/0187308 | A1 | 7/2012 | Evers |
| 2014/0161665 | A1 | 6/2014 | Evers |
| 2015/0190541 | A1* | 7/2015 | Kitamura .............. A61L 2/07 422/26 |

* cited by examiner

SYSTEMS AND METHODS FOR STERILIZING SEALED RADIONUCLIDE GENERATOR COLUMN ASSEMBLIES

CROSS-REFERENCE TO RELATED APPLICATIONS

This application claims priority to U.S. Provisional Patent Application Ser. No. 62/331,616, filed May 4, 2016, the disclosure of which is hereby incorporated by reference in its entirety.

FIELD

The field of the disclosure relates generally to radionuclide generators and, more particularly, to systems and methods for sterilizing sealed radionuclide generator column assemblies.

BACKGROUND

Radioactive material is used in nuclear medicine for diagnostic and therapeutic purposes by injecting a patient with a small dose of the radioactive material, which concentrates in certain organs or regions of the patient. Radioactive materials typically used for nuclear medicine include Technetium-99m ("Tc-99m"), Indium-111m ("In-111"), Thallium-201, and Strontium-87m, among others.

Such radioactive materials may be produced using a radionuclide generator. Radionuclide generators generally include a column that has media for retaining a long-lived parent radionuclide that spontaneously decays into a daughter radionuclide that has a relatively short half-life. The column may be incorporated into a column assembly that has a needle-like outlet port that receives an evacuated vial to draw saline or other eluant liquid, provided to a needle-like inlet port, through a flow path of the column assembly, including the column itself. This liquid may elute and deliver daughter radionuclide from the column and to the evacuated vial for subsequent use in nuclear medical imaging applications, among other uses.

Prior to use in medical applications, radionuclide generators are sterilized such that when sterile eluant is eluted through the device, the resulting elution is also sterile and suitable for injection into a patient. At least some known sterilization methods use a vented column assembly for the sterilization process. The use of vented column assemblies increases the risks of radiological material (e.g., radiologically contaminated steam) being released from the column assembly, and moisture generated during the sterilization process re-entering the fluid line of the column assembly. In some instances, vented caps or covers are used to cover the outlet port of the elution assemblies to inhibit moisture from re-entering the column assembly. Such caps can increase the cost and complexity of the sterilization process. Accordingly, a need exists for improved systems and methods for sterilizing radionuclide generator column assemblies.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

One aspect is a method of sterilizing a column assembly that includes a column having an interior containing a retaining media and a parent radionuclide retained by the retaining media. An inlet port is connected with the interior of the column, and an outlet port is connected with the interior of the column. The method includes sealing at least one of the inlet port and the outlet port to form a sealed column assembly such that fluid communication with the column interior though both the inlet port and the outlet port is prevented, and sterilizing the sealed column assembly to form a terminally-sterilized column assembly.

In another aspect, a system includes a sterilizer defining a sterilization chamber, and a sealed column assembly is disposed within the sterilization chamber. The column assembly includes a column having an interior containing a retaining media and a parent radionuclide retained by the retaining media, and an elution flow path including an inlet line and an outlet line. Each of the inlet and outlet lines is in fluid communication with the interior of the column. The elution flow path is completely sealed such that fluid flow through the column interior is prevented.

In yet another aspect, a method includes providing a sealed radionuclide generator column assembly including a column having an interior that contains a retaining media and a parent radionuclide retained by the retaining media. An elution flow path of the sealed column assembly is completely sealed such that fluid flow through the column interior is prevented. The method further includes placing the sealed column assembly within a sterilization chamber of a sterilizer, and sterilizing the sealed column assembly to produce a terminally-sterilized, sealed column assembly.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Figure 1:
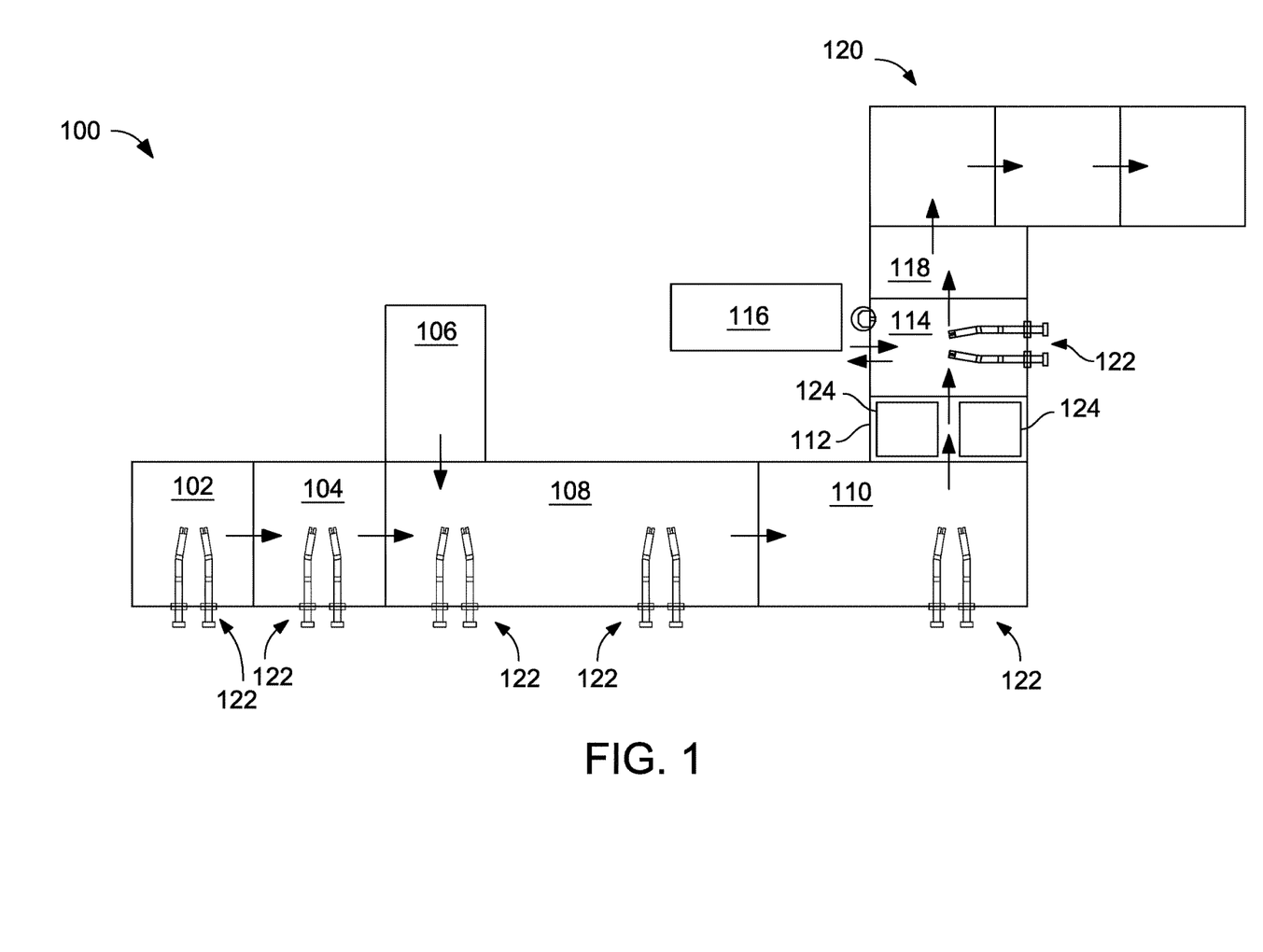
FIG. 1 is a schematic view of a system for producing radionuclide generators.

FIG. 1 is a schematic view of a system 100 for manufacturing radionuclide generators. The system 100 shown in FIG. 1 may be used to produce various radionuclide generators, including, for example and without limitation, Technetium generators, Indium generators, and Strontium generators. The system 100 of FIG. 1 is particularly suited for producing Technetium generators. A Technetium generator is a pharmaceutical drug and device used to create sterile injectable solutions containing Tc-99m, an agent used in diagnostic imaging with a relatively short 6 hour radiological half-life, allowing the Tc-99m to be relatively quickly eliminated from human tissue. Tc-99m is "generated" via the natural decay of Molybdenum ("Mo-99"), which has a 66 hour half-life, which is desirable because it gives the generator a relatively long two week shelf life. During generator operation (i.e., elution with a saline solution), Mo-99 remains chemically bound to a core alumina bed (i.e., a retaining media) packed within the generator column, while Tc-99m washes free into an elution vial, ready for injection into a patient. While the system 100 is described herein with reference to Technetium generators, it is understood that the system 100 may be used to produce radionuclide generators other than Technetium generators.

As shown in FIG. 1, the system 100 generally includes a plurality of stations. In the example embodiment, the system 100 includes a cask loading station 102, a formulation station 104, an activation station 106, a fill/wash station 108, an assay/autoclave loading station 110, an autoclave station 112, an autoclave unloading station 114, a quality control testing station 116, a shielding station 118, and a packaging station 120.

The cask loading station 102 is configured to receive and handle casks or containers of radioactive material, such as a parent radionuclide, and transfer the radioactive material to the formulation station 104. Radioactive material may be transported in secondary containment vessels and flasks that need to be removed from an outer cask prior to formulation. The cask loading station 102 includes suitable tooling and mechanisms to extract secondary containment vessels and flasks from outer casks, as well as transfer of flasks to the formulation cell. Suitable devices that may be used in the cask loading station 102 include, for example and without limitation, telemanipulators 122.

At the formulation station 104, the raw radioactive material (i.e., Mo-99) is quality control tested, chemically treated if necessary, and then pH adjusted while diluting the raw radioactive material to a desired final target concentration. The formulated radioactive material is stored in a suitable containment vessel (e.g., within the formulation station 104).

Column assemblies containing a column of retaining media (e.g., alumina) are activated at the activation station 106 to facilitate binding of the formulated radioactive material with the retaining media. In some embodiments, column assemblies are activated by eluting the column assemblies with a suitable volume of HCl at a suitable pH level. Column assemblies are held for a minimum wait time prior to charging the column assemblies with the parent radionuclide.

Following activation, column assemblies are loaded into the fill/wash station 108 using a suitable transfer mechanism (e.g., transfer drawer). Each column assembly is then charged with parent radionuclide by eluting formulated radioactive solution (e.g., Mo-99) from the formulation station 104 through individual column assemblies using suitable liquid handling systems (e.g., pumps, valves, etc.). The volume of formulated radioactive solution eluted through each column assembly is based on the desired Curie (Ci) activity for the corresponding column assembly. The volume eluted through each column assembly is equivalent to the total Ci activity identified at the time of calibration for the column assembly. For example, if a volume of formulated Mo-99 required to make a 1.0 Ci generator (at time of calibration) is 'X', the volume required to make a 19.0 Ci generator is simply 19 times X. After a minimum wait time, the charged column assemblies are eluted with a suitable volume and concentration of acetic acid, followed by an elution with a suitable volume and concentration of saline to "wash" the column assemblies. Column assemblies are held for a minimum wait time before performing assays on the column assemblies.

The charged and washed column assemblies are then transferred to the assay/autoclave load station 110, in which assays are taken from each column assembly to check the amount of parent and daughter radionuclide produced during elution. Each column assembly is eluted with a suitable volume of saline, and the resulting solution is assayed to check the parent and daughter radionuclide levels in the assay. Where the radioactive material is Mo-99, the elutions are assayed for both Tc-99m and Mo-99. Column assemblies having a daughter radionuclide (e.g., Tc-99m) assay falling outside an acceptable range calculation are rejected. Column assemblies having a parent radionuclide (e.g., Mo-99) breakthrough exceeding a maximum acceptable limit are also rejected.

Following the assay process, tip caps are applied to the outlet port and the fill port of the column assembly. Column assemblies may be provided with tip caps already applied to the inlet port. If the column assembly is not provided with a tip cap pre-applied to the inlet port, a tip cap may be applied prior to, subsequent to, or concurrently with tip caps being applied to the outlet port and the fill port. Assayed, tip-capped column assemblies are then loaded into an autoclave sterilizer 124 located in the autoclave station 112 for terminal sterilization. The sealed column assemblies are subjected to an autoclave sterilization process within the autoclave station 112 to produce terminally-sterilized column assemblies.

Following the autoclave sterilization cycle, column assemblies are unloaded from the autoclave station 112 into the autoclave unloading station 114. Column assemblies are then transferred to the shielding station 118 for shielding.

Some of the column assemblies are transferred to the quality control testing station 116 for quality control. In the example embodiment, the quality control testing station 116 includes a QC testing isolator that is sanitized prior to QC testing, and maintained at a positive pressure and a Grade A clean room environment to minimize possible sources of contamination. Column assemblies are aseptically eluted for in-process QC sampling, and subjected to sterility testing within the isolator of the quality control testing station 116. Tip caps are reapplied to the inlet and outlet needles of the column assemblies before the column assemblies are transferred back to the autoclave unloading station 114.

The system 100 includes a suitable transfer mechanism for transferring column assemblies from the autoclave unloading station 114 (which is maintained at a negative pressure differential, Grade B clean room environment) to the isolator of the quality control testing station 116. In some embodiments, column assemblies subjected to quality control testing may be transferred from the quality control testing station 116 back to the autoclave unloading station 114, and can be re-sterilized and re-tested, or re-sterilized and packaged for shipment. In other embodiments, column assemblies are discarded after being subjected to QC testing.

In the shielding station 118, column assemblies from the autoclave unloading station 114 are visually inspected for container closure part presence, and then placed within a radiation shielding container (e.g., a lead plug). The radiation shielding container is inserted into an appropriate safe constructed of suitable radiation shielding material (e.g., lead, tungsten or depleted uranium). Shielded column assemblies are then released from the shielding station 118.

In the packaging station 120, shielded column assemblies from the shielding station 118 are placed in buckets pre-labeled with appropriate regulatory (e.g., FDA) labels. A label uniquely identifying each generator is also printed and applied to each bucket. A hood is then applied to each bucket. A handle is then applied to each hood.

The system 100 may generally include any suitable transport systems and devices to facilitate transferring column assemblies between stations. In some embodiments, for example, each of the stations includes at least one telemanipulator 122 to allow an operator outside the hot cell environment (i.e., within the surrounding room or lab) to manipulate and transfer column assemblies within the hot cell environment. Moreover, in some embodiments, the system 100 includes a conveyance system to automatically transport column assemblies between the stations and/or between substations within one or more of the stations (e.g., between a fill substation and a wash substation within the fill/wash station 108).

In the example embodiment, some stations of the system 100 include and/or are enclosed within a shielded nuclear radiation containment chamber, also referred to herein as a "hot cell". Hot cells generally include an enclosure constructed of nuclear radiation shielding material designed to shield the surrounding environment from nuclear radiation. Suitable shielding materials from which hot cells may be constructed include, for example and without limitation, lead, depleted uranium, and tungsten. In some embodiments, hot cells are constructed of steel-clad lead walls forming a cuboid or rectangular prism. In some embodiments, a hot cell may include a viewing window constructed of a transparent shielding material. Suitable materials from which viewing windows may be constructed include, for example and without limitation, lead glass. In the example embodiment, each of the cask loading station 102, the formulation station 104, the fill/wash station 108, the assay/autoclave loading station 110, the autoclave station 112, the autoclave unloading station 114, and the shielding station 118 include and/or are enclosed within a hot cell.

In some embodiments, one or more of the stations are maintained at a certain clean room grade (e.g., Grade B or Grade C). In the example embodiment, pre-autoclave hot cells (i.e., the cask loading station 102, the formulation station 104, the fill/wash station 108, the assay/autoclave loading station 110) are maintained at a Grade C clean room environment, and the autoclave unloading cell or station 114 is maintained at a Grade B clean room environment. The shielding station 118 is maintained at a Grade C clean room environment. The packaging stations 120 are maintained at a Grade D clean room environment. Unless otherwise indicated, references to clean room classifications refer to clean room classifications according to Annex 1 of the European Union Guidelines to Good Manufacturing Practice.

Additionally, the pressure within one or more stations of the system 100 may be controlled at a negative or positive pressure differential relative to the surrounding environment and/or relative to adjacent cells or stations. In some embodiments, for example, all hot cells are maintained at a negative pressure relative to the surrounding environment. Moreover, in some embodiments, the isolator of the quality control testing station 116 is maintained at a positive pressure relative to the surrounding environment and/or relative to adjacent stations of the system 100 (e.g., relative to the autoclave unloading station 114).

Figure 2:
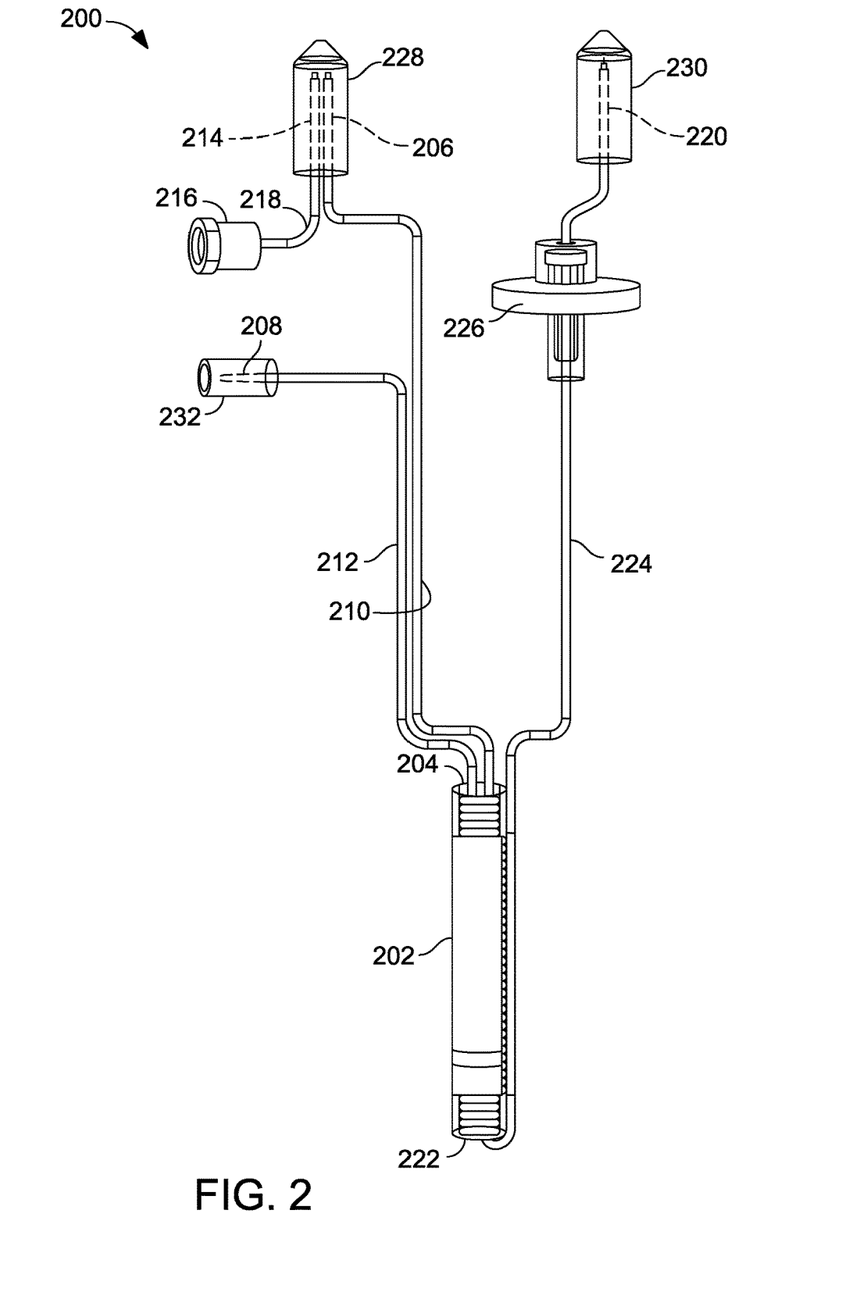
FIG. 2 is a perspective view of a column assembly of a radionuclide generator.

FIG. 2 is a perspective view of an example elution column assembly 200 that may be produced with the system 100. As shown in FIG. 2, the column assembly 200 includes an elution column 202 fluidly connected at a top end 204 to an inlet port 206 and a charge port 208 through an inlet line 210 and a charge line 212, respectively. A vent port 214 that communicates fluidly with an eluant vent 216 via a venting conduit 218 is positioned adjacent to the inlet port 206, and may, in operation, provide a vent to a vial or bottle of eluant connected to the inlet port 206. The column assembly 200 also includes an outlet port 220 that is fluidly connected to a bottom end 222 of the column 202 through an outlet line 224. A filter assembly 226 is incorporated into the outlet line 224. The column 202 defines a column interior that includes a retaining media (e.g., alumina beads, not shown). As described above, during production of the column assembly 200, the column 202 is charged via the charge port 208 with a radioactive material, such as Molybdenum-99, which is retained with the interior of the column 202 by the retaining media. The radioactive material retained by the retaining media is also referred to herein as the "parent radionuclide".

During use of the column assembly 200, an eluant vial (not shown) containing an eluant fluid (e.g., saline) is connected to the inlet port 206 by piercing a septum of the eluant vial with the needle-like inlet port 206. An evacuated elution vial (not shown) is connected to the outlet port 220 by piercing a septum of the elution vial with the needle-like outlet port 220. Eluant fluid from the eluant vial is drawn through the elution line, and elutes the column 202 containing parent radionuclide (e.g., Mo-99). The negative pressure of the evacuated vial draws eluant from the eluant vial and through the flow pathway, including the column, to elute daughter radionuclide (e.g., Tc-99m) for delivery through the outlet port 220 and to the elution vial. The eluant vent 216 allows air to enter the eluant vial through the vent port 214 to prevent a negative pressure within the eluant vial that might otherwise impede the flow of eluant through the flow pathway. After having eluted daughter radionuclide from the column 202, the elution vial is removed from the outlet port 220.

The column assembly 200 shown in FIG. 2 is shown in a finally assembled state. In particular, the column assembly 200 includes an inlet cap 228, an outlet cap 230, and a charge port cap 232. The caps 228, 230, 232 protect respective ports 206, 214, 220, and 208, and inhibit contaminants from entering the column assembly 200 via the needles. In prior radionuclide generator production processes, needle closure is applied after a sterilization process such that the column assembly is vented during the sterilization process.

Prior to final packaging, elution column assemblies of radionuclide generators intended for use in the medical industry are sterilized such that when sterile eluant is eluted through the device, the resulting elution is also sterile and suitable for injection into a patient. Known methods of sterilizing column assemblies include aseptic assembly, and autoclave sterilization of a vented column assembly. Aseptic assembly generally includes sterilizing components of the column assembly separately, and subsequently assembling the column assembly in an aseptic environment. Autoclave sterilization generally includes exposing a vented column assembly, having a column loaded with parent radionuclide, to a saturated steam, or a steam-air mixture environment.

Autoclave sterilization provides advantages over aseptic assembly because it enables production of a terminally sterilized generator. In other words, autoclave sterilization produces a generator assembly that is sterilized in its final container, or at least that is sterilized with the flow path between the inlet port, the column, and the outlet port (i.e., the elution flow path) assembled in its final form, including any vented or non-vented caps over the inlet and outlet ports. Terminal sterilization provides significantly greater sterility assurance than aseptic assembly. As noted above, known methods of autoclave sterilization include exposing a vented column assembly to a saturated steam or a steam-air mixture environment. During this process, liquid that resides in the column assembly, including the column and tubes that extend between the column and the inlet and outlet ports may be heated to vapor form (e.g., steam) to kill and/or inactivate contaminants. The vent allows the introduction of steam and the release of vapors from the column during the sterilization process. However, because the column assembly is vented, radiological material (e.g., radiologically contaminated steam) may be released from the column assembly, and/or moisture generated during the sterilization process may re-enter the fluid line of the column assembly, which may adversely affect generator performance.

A completely sealed, terminally-sterilized generator column assembly and systems and methods for producing completely sealed, terminally-sterilized generator column assemblies are disclosed.

Figure 3:
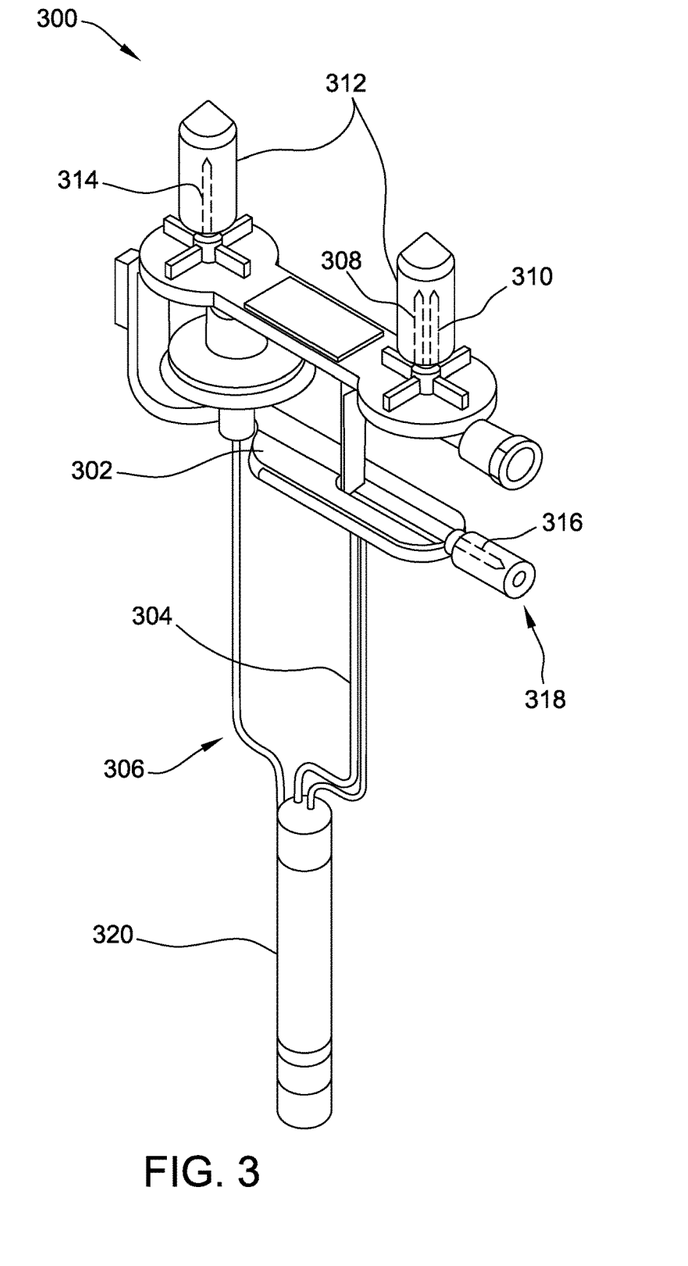
FIG. 3 is a perspective view of a fully sealed, terminally-sterilized column assembly.

FIG. 3 is a perspective view of a completely sealed, terminally-sterilized generator column assembly 300, with a U-shaped elution line support 302, which supports the inlet and outlet lines 304, 306 and ports of the column assembly 300.

A needle-like inlet port 308 and vent 310 of the column assembly 300 are covered and completely sealed by one of two cap plugs 312, and a needle-like outlet port 314 of the column assembly 300 is covered by the other of the cap plugs 312. Each of the cap plugs 312 is a solid, non-hollow, single-piece member constructed of an elastomeric material that is pierceable by the needle-like ports of the column assembly 300. The cap plugs 312 are constructed of a suitably elastomeric material such that when one of the needle-like ports of the column assembly 300 pierces one of the cap plugs 312, the cap plug 312 seals off the corresponding port. Suitable materials from which the cap plugs 312 may be constructed include, for example and without limitation, silicone. One particularly suitable material from which cap plugs 312 may be constructed is the commercially available silicone rubber sold by Wacker Chemie AG under the trade name Elastosil® 3003LR/20.

A needle-like fill or charge port 316 is covered by a fill port stopper 318. The fill port stopper 318 may be constructed of the same or similar materials as the cap plugs 312. One particularly suitable material from which the fill port stopper 318 may be constructed is the commercially available silicone rubber sold by Wacker Chemie AG under the trade name Elastosil® 3003LR/50.

A suitable method of producing the completely sealed, terminally-sterilized generator column assembly 300 of FIG. 3 includes completely sealing the elution flow path (including the inlet port 308, the inlet line 304, the outlet line 306, and the outlet port 314) of the column assembly 300 such that no fluid flow is permitted through the column 320 of the column assembly 300, and subjecting the sealed column assembly 300 to a sterilization process. In some embodiments, sealing the elution flow path of the column assembly 300 includes sealing each of the needle-like inlet and outlet ports 308, 314 of the column assembly 300 using, for example, the cap plugs 312. For example, with additional reference to FIG. 1, a cap plug 312 is placed over the outlet port 314 and/or a inlet port 308 of the column assembly 300 at the assay/autoclave loading station 110. The system 100 may include a dedicated capping station that uses automated or semi-automated tooling (e.g., telemanipulators) to apply the cap plugs 312 to the inlet port 308 and/or the outlet port 314 of the column assembly 300. Such a capping station may be located, for example, between an assay substation and an autoclave loading substation within the assay/autoclave loading station 110. In some embodiments, column assemblies may be provided with cap plugs 312 already applied to the inlet port 308. In such embodiments, a cap plug is not applied to the inlet port 308 at the assay/autoclave loading station 110.

The method may also include sealing the charge or fill port 316 of the column assembly 300 using, for example, the fill port stopper 318. Referring again to FIG. 1, the fill port stopper 318 may be applied to the needle-like fill port 316 of the column assembly 300 after the assay process performed at the assay/autoclave loading station 110. The fill port stopper 318 may be applied to the column assembly 300 simultaneously with the outlet cap plug 312, before the outlet cap plug 312 is applied, or after the outlet cap plug 312 is applied to the column assembly 300. The fill port stopper 318 may be applied to the column assembly 300 within a capping station of the system 100 using automated or semi-automated tooling (e.g., a telemanipulator).

When the cap plugs 312 and fill port stopper 318 are applied to the respective inlet and outlet ports 308, 314, and the fill port 316 of the column assembly 300, the column assembly 300 is completely sealed. That is, no fluid flow is permitted through the elution flow path, or through the interior of the column 320. In other words, fluid communication with the interior of the column 320 (and the parent radionuclide contained therein) is prevented.

The completely sealed column assembly 300 is then subjected to a sterilization process that results in a completely sealed, terminally-sterilized column assembly 300. The sterilization process may be carried out in an autoclave sterilizer (e.g., sterilizer 124) located, for example, between the assay/autoclave loading station 110 and the autoclave unloading station 114 (shown in FIG. 1). The sterilization processes described herein may be performed in commercially available autoclave sterilizers, including, for example and without limitation, PST-series sterilizers available from Belimed.

Figure 4:
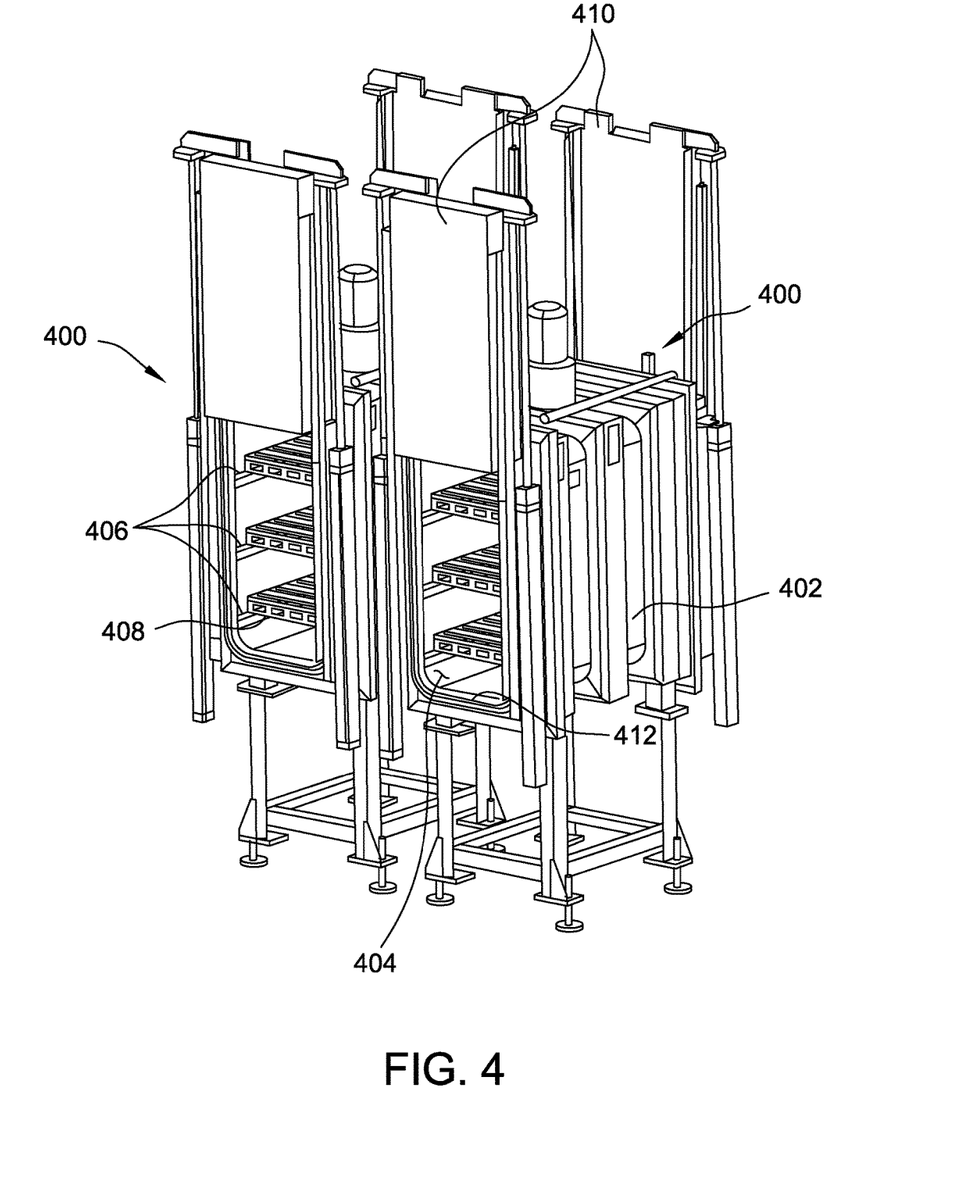
FIG. 4 is a perspective view of two example autoclave sterilizers suitable for use in the system of FIG. 1.
Figure 5:
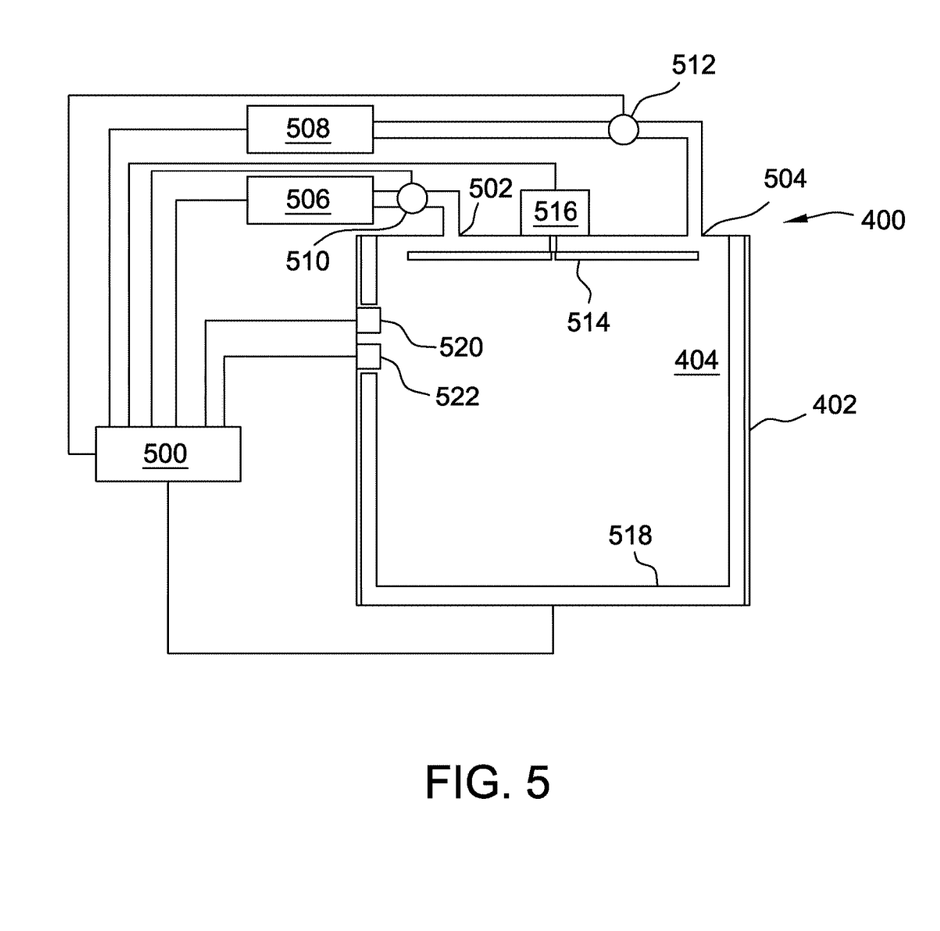
FIG. 5 is a schematic view of one of the autoclave sterilizers of FIG. 4 connected to a controller.

FIG. 4 is a perspective view of two example autoclave sterilizers 400 suitable for use in the system 100 of FIG. 1, and for carrying out the methods described herein. FIG. 5 is a schematic view of one of the autoclave sterilizers 400 connected to a controller 500 for controlling operation of the sterilizer 400.

As shown in FIG. 4, each of the sterilizers 400 includes a generally rectangular enclosure 402 defining a sterilization chamber 404 in which a sterilization process is performed. In this embodiment, the enclosures 402 are made of stainless steel, specifically, 316L stainless steel, although the enclosures may be constructed of any other suitable material that enables the system 100 to function as described herein. In some embodiments, the sterilizers 400 and/or the enclosures 402 are positioned within a radiological containment chamber (i.e., a hot cell) to provide radiation shielding.

In this embodiment, each of the enclosures 402 includes a plurality of tracks or rails 406 located within the sterilization chamber 404. The rails 406 are vertically spaced within the sterilization chamber 404, and are configured to receive carts 408 carrying racks (not shown in FIG. 4) of radionuclide generator column assemblies.

Each of the sterilizers 400 also includes two sealing doors 410 located on opposite sides of the respective enclosure 402 for sealing access openings 412 to the sterilization chamber 404. In this embodiment, the sealing doors 410 are guillotine-style sealing doors, although the sealing doors 410 may have any other suitable configuration that enables the system 100 to function as described herein.

Referring to FIG. 5, each of the autoclave sterilizers 400 includes a steam inlet 502 for introducing saturated steam into the sterilization chamber 404, and a compressed air inlet 504 for introducing compressed air into the sterilization chamber 404. A steam generator 506 is connected to the steam inlet 502, and a compressor 508 is connected to the compressed air inlet 504. The steam generator 506 generally includes a clean steam generator, such as a commercially available clean steam generator. In some embodiments, the autoclave sterilizers 400 include an insitu filter (not shown) for filtering compressed air before it is introduced into the sterilization chamber 404 through compressed air inlet 504.

The autoclave sterilizers 400 also include a steam inlet valve 510 (generally, a first valve) connected between the steam generator 506 and the steam inlet 502 to control the supply of saturated steam into the sterilization chamber 404, and a compressed air inlet valve 512 (generally, a second valve) connected between the compressor 508 and the compressed air inlet 504 to control the supply of compressed air into the sterilization chamber 404. The steam inlet valve 510 and the compressed air inlet valve 512 may generally include any suitable actuatable valves that enable the autoclave sterilizers 400 to function as described herein, including, for example and without limitation, electrically-actuated valves and pneumatically actuated valves. Each of the steam inlet valve 510 and the compressed air inlet valve 512 is connected to the controller 500 for controlling operation of the respective valves.

The autoclave sterilizers 400 also include a fan 514 for mixing steam and compressed air within the sterilization chamber 404. A motor 516 is connected to the fan 514 for controlling operation thereof. In this embodiment, the fan 514 is mounted to a top or ceiling of the enclosure 402, proximate to the steam inlet 502 and compressed air inlet 504.

In this embodiment, each of the autoclave sterilizers 400 also includes a steam jacket 518 for controlling the temperature of the sterilization chamber 404. The steam jacket 518 is fluidly connected to source of pressurized steam, and is filled with pressurized steam to insulate the sterilization chamber 404 and facilitate maintaining a relatively constant temperature within the sterilization chamber 404.

The sterilizers 400 may also include one or more sensors for monitoring conditions within the sterilization chamber 404. In this embodiment, each of the autoclave sterilizers 400 includes a temperature sensor 520 and a pressure sensor 522. The temperature sensor 520 and the pressure sensor 522 are connected to the controller 500 for providing feedback to the controller 500 about temperature and pressure conditions within the autoclave sterilizer 400. The temperature sensor 520 may be any suitable temperature sensor that enables the sterilizer 400 to function as described herein including, for example and without limitation, a resistance temperature detector. The pressure sensor 522 may be any suitable pressure sensor that enables the sterilizer 400 to function as described herein. In some embodiments, the pressure sensor 522 is a pressure transducer.

The controller 500 is connected to each of the steam inlet valve 510, the compressed air inlet valve 512, and the fan motor 516 for controlling operation of the respective components. Also, as noted above, the controller 500 is connected to the temperature and pressure sensors 516 and 518 for monitoring temperature and pressure conditions within the sterilization chamber 404. In the example embodiment, the controller 500 is also connected to the steam generator 506 and the compressor 508 to control operation of the steam generator 506 and the compressor 508.

The controller 500 is configured to control operation of at least the steam inlet valve 510 and the compressed air inlet valve 512 in response to temperature and pressure measurements received from the temperature sensor 520 and the pressure sensor 522, respectively. Specifically, the controller 500 controls the position and/or regulates each of the steam inlet valve 510 and the compressed air inlet valve 512 to control the supply of saturated steam and compressed air, respectively, into the sterilization chamber 404.

Figure 6:
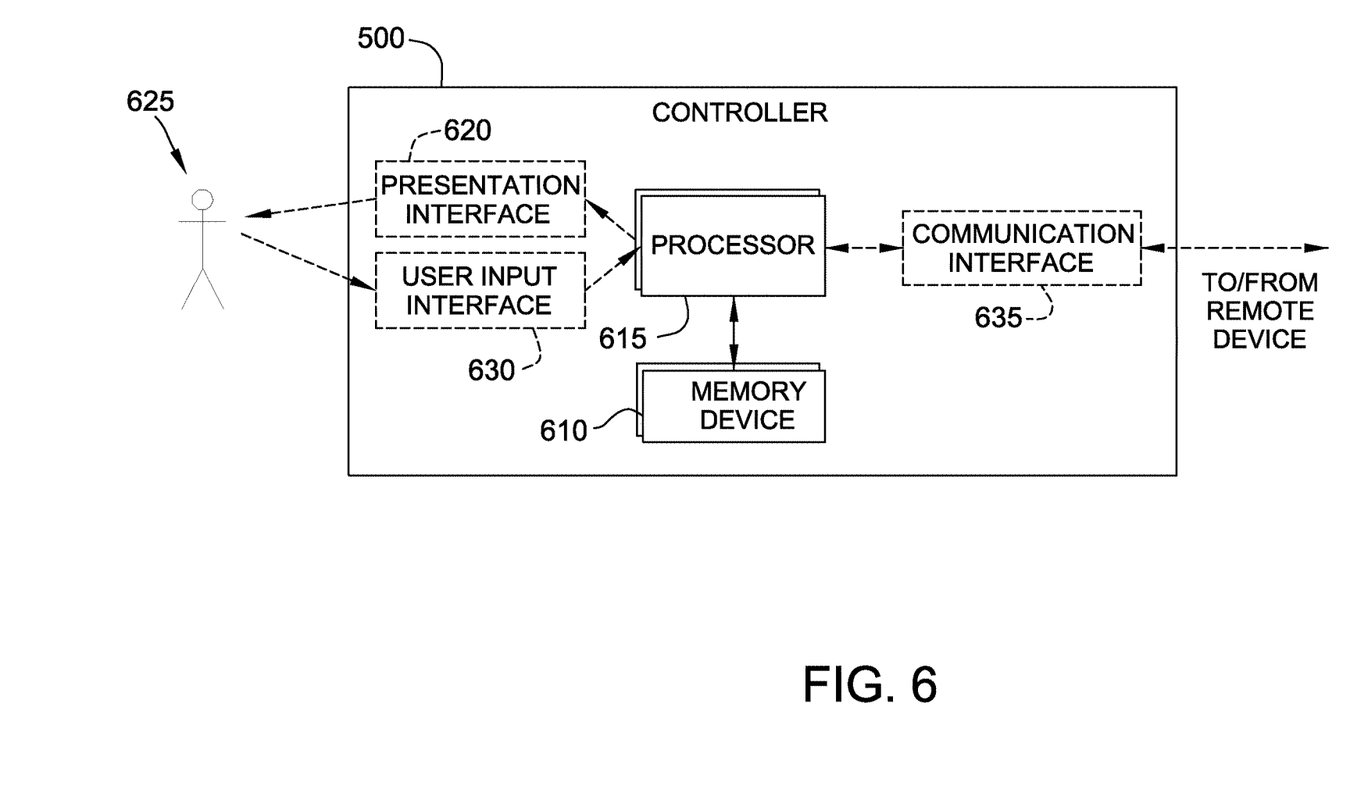
FIG. 6 is a block diagram of the controller shown in FIG. 5.

FIG. 6 is a block diagram of the controller 500. The controller 500 may have any suitable controller configuration that enables the sterilizer 400 to function as described herein. In some embodiments, for example, the controller 500 is a PID controller. In this embodiment, the controller 500 includes at least one memory device 610 and a processor 615 that is coupled to the memory device 610 for executing instructions. In this embodiment, executable instructions are stored in the memory device 610, and the controller 500 performs one or more operations described herein by programming the processor 615. For example, the processor 615 may be programmed by encoding an operation as one or more executable instructions and by providing the executable instructions in the memory device 610.

The processor 615 may include one or more processing units (e.g., in a multi-core configuration). Further, the processor 615 may be implemented using one or more heterogeneous processor systems in which a main processor is present with secondary processors on a single chip. As another illustrative example, the processor 615 may be a symmetric multi-processor system containing multiple processors of the same type. Further, the processor 615 may be implemented using any suitable programmable circuit including one or more systems and microcontrollers, microprocessors, programmable logic controllers (PLCs), reduced instruction set circuits (RISC), application specific integrated circuits (ASIC), programmable logic circuits, field programmable gate arrays (FPGA), and any other circuit capable of executing the functions described herein. In this embodiment, the processor 615 controls operation of the autoclave sterilizer 400 by outputting control signals to at least the steam inlet valve 510, the compressed air inlet valve 512, and the fan motor 516. Further, in this embodiment, the processor 615 receives signals from the temperature sensor 520 and the pressure sensor 522 associated with the temperature and pressure, respectively, within the sterilization chamber 404.

The memory device 610 is one or more devices that enable information such as executable instructions and/or other data to be stored and retrieved. The memory device 610 may include one or more computer readable media, such as, without limitation, dynamic random access memory (DRAM), static random access memory (SRAM), a solid state disk, and/or a hard disk. The memory device 610 may be configured to store, without limitation, application source code, application object code, source code portions of interest, object code portions of interest, configuration data, execution events and/or any other type of data.

In this embodiment, the controller 500 includes a presentation interface 620 that is connected to the processor 615. The presentation interface 620 presents information, such as application source code and/or execution events, to a user 625, such as a technician or operator. For example, the presentation interface 620 may include a display adapter (not shown) that may be coupled to a display device, such as a cathode ray tube (CRT), a liquid crystal display (LCD), an organic LED (OLED) display, and/or an "electronic ink" display. The presentation interface 620 may include one or more display devices.

The controller 500 also includes a user input interface 630 in this embodiment. The user input interface 630 is connected to the processor 615 and receives input from the user 625. The user input interface 630 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of the presentation interface 620 and the user input interface 630. In this embodiment, the user input interface 630 receives inputs associated with a desired exposure temperature, a desired exposure pressure, and a desired exposure time.

In this embodiment, the controller 500 further includes a communication interface 635 connected to the processor 615. The communication interface 635 communicates with one or more remote devices, such as the temperature sensor 520 and the pressure sensor 522.

In use, the sterilization process generally includes positioning the sealed column assembly 300 within the sterilization chamber 404 of the autoclave sterilizer 400, sealing the sterilization chamber 404, raising the temperature and pressure within the sterilization chamber 404 to a desired exposure temperature and exposure pressure, and exposing the sealed column assembly 300 to a mixture of steam and compressed air (also referred to as the "exposure phase").

The sealed column assembly 300 is exposed to the steam-air mixture for a suitable amount of time and at a suitable exposure temperature and pressure that enables the external surfaces of the needle-like ports, which are covered by the cap plugs 312 and the fill port stopper 318, to be sterilized, while matching chamber pressure with pressure formed within the sealed column assembly. In some embodiments, the exposure phase may be carried out at an exposure temperature of at least 100° C., at least 110° C., at least 120° C., at least 122° C., at least 124° C., at least 126° C., at least 128° C., at least 130° C., and even up to 140° C. In some embodiments, the exposure phase is carried out at an exposure temperature of between about 110° C. and about 130° C. In other embodiments, the exposure phase is carried out at an exposure temperature of between about 120° C. and about 140° C. In yet other embodiments, the exposure phase is carried out at an exposure temperature of between about 120° C. and about 130° C.

In some embodiments, the exposure phase may be carried out at an exposure pressure of at least 2000 millibars (mbar), at least 2500 mbar, at least 2700 mbar, at least 2900 mbar, at least 3000 mbar, at least 3050 mbar, at least 3075 mbar, at least 3100 mbar, and even up to 3200 mbar. In some embodiments, the exposure phase is carried out at an exposure pressure of between about 2900 mbar and about 3200 mbar. In other embodiments, the exposure phase is carried out at an exposure pressure of between about 2800 mbar and about 3100 mbar. In yet other embodiments, the exposure phase is carried out at an exposure pressure of between about 3000 mbar and about 3100 mbar.

Referring to FIGS. 4 and 5, the controller 500 may control the steam inlet valve 510 and the compressed air inlet valve 512 to raise the pressure and temperature within the sterilization chamber 404 to the desired exposure pressure and desired exposure temperature. In this embodiment, the controller 500 controls the steam inlet valve 510 by opening the steam inlet valve 510 to allow high temperature, saturated steam to enter the sterilization chamber 404 through the steam inlet 502, thereby raising the temperature of the sterilization chamber 404 to the desired exposure temperature. The controller 500 receives temperature feedback from the temperature sensor 520, and closes and/or regulates the steam inlet valve 510 once the desired exposure temperature is reached. Further, in this embodiment, the controller receives pressure measurements from the pressure sensor 522, and controls the compressed air inlet valve 512 to control chamber pressure to match the calculated pressure inside a sealed generator column assembly to balance pressures inside and outside the column assembly to prevent the column assembly from rupturing.

The sealed column assembly 300 is exposed to the steam-air mixture environment for a suitable time that results in sterilization of all components and surfaces of the sealed column assembly 300, including the internal and external surfaces of the needle-like ports that are covered by the cap plugs 312 and the fill port stopper 318. In some embodiments, for example, the sealed column assembly 300 is exposed to the steam-air mixture environment for at least 10 minutes, at least 15 minutes, at least 20 minutes, at least 25 minutes, at least 30 minutes, at least 35 minutes, and even up to 45 minutes. In some embodiments, the sealed column assembly 300 is exposed to the steam-air mixture environment for an exposure time of between about 15 minutes and about 45 minutes, and, more suitably, for an exposure time of between about 20 minutes and about 40 minutes.

In this embodiment, the steam-air mixture is formed in the sterilization chamber 404 by introducing sterile compressed air into the sterilization chamber 404 through the compressed air inlet 504, and mixing the compressed air with steam introduced into the sterilization chamber 404 via the steam inlet 502. In some embodiments, for example, regulated compressed air is fed through a sterile insitu filter into the sterilization chamber 404, and homogeneously mixed with saturated steam (introduced from the steam inlet 502) with the internal fan 514.

In some embodiments, the rate at which the compressed air is introduced into the sterilization chamber 404 is controlled at a rate to maintain a partial pressure around the sealed column assembly at a pressure substantially equal to a partial pressure within the sealed column assembly. For example, suitable set-point pressures at which the sterilization process should be carried to prevent physical deformation of the column assembly may be experimentally determined. These values may be stored in the controller 500 (specifically, in the memory device 610 of the controller 500). The sterilization chamber pressure is then monitored using suitable pressure sensors or monitors (e.g., pressure sensor 522), and the rate at which compressed air is introduced into the sterilization chamber 404 is controlled using the controller 500 based on the sensed pressure within the sterilization chamber 404. For example, if the sensed pressure within the sterilization chamber 404 is too low (e.g., more than 30 mbar below the set-point pressure), compressed air is added, for example, by the controller 500 opening and/or regulating the compressed air inlet valve 512 until the sensed pressure reaches the set-point pressure. Further, if the sensed pressure within the sterilization chamber exceeds the set-point pressure by a preset threshold (e.g., more than 60 mbar above the set-point pressure), the flow of compressed air to the sterilization chamber 404 is terminated.

In some embodiments, the sterilization process also includes monitoring the temperature within the sterilization chamber 404, and controlling the flow of saturated steam to the sterilization chamber 404 to adjust the temperature. In this embodiment, for example, the temperature within the sterilization chamber 404 is measured using the temperature sensor 520, and if the measured temperature is below a threshold temperature, high temperature saturated steam is added to the sterilization chamber 404. In this embodiment, the flow of steam to the sterilization chamber 404 is controlled by the controller 500, specifically, by controlling the steam inlet valve 510.

In some embodiments, more than one sealed column assembly is sterilized at a time. In one embodiment, for example, up to 192 column assemblies are loaded into the sterilization chamber 404 of the autoclave sterilizer 400, and simultaneously subjected to a sterilization process.

One example method of sterilizing a completely sealed column assembly includes:
a) loading a plurality of column assemblies into the sterilization chamber of an autoclave sterilizer;
b) gradually heating the sterilization chamber to an exposure temperature of between about 122° C. and about 130° C., while simultaneously raising the pressure in the sterilization chamber to an exposure pressure of between about 2800 mbar and about 3200 mbar;
c) introducing compressed sterile air into the sterilization chamber and homogenously mixing the sterile air within the chamber to create a partial pressure equal to the pressure within the sealed column assemblies to prevent the column assemblies from rupturing;
d) allowing the sterilization chamber temperature to stabilize for a stabilization period of between about 3 minutes and about 10 minutes;
e) exposing the column assemblies to a steam-air mixture environment for an exposure time of at least 30 minutes;
f) gradually cooling the sterilization chamber to a final temperature below 90° C., more suitably between about 50° C. and about 70° C., and
g) removing the plurality of sealed column assemblies from the sterilization chamber.

In some embodiments, the autoclave end-of-cycle $F_O$ values are at least 40 minutes, at least 50 minutes, at least 60 minutes, at least 70 minutes, at least 80 minutes, at least 90 minutes, and even up to 120 minutes. By general comparison, end-of-cycle $F_O$ values for previous autoclave sterilization processes are less than 20 minutes. The term "$F_O$ value" refers to the number of equivalent minutes of steam sterilization at 250° F. (121° C.) delivered to a load or product (e.g., a column assembly). For example, if a cycle has an $F_O$ value of 12, the sterilization effectiveness of that cycle is equal to 12 minutes at 250° F. (121° C.) regardless of the process temperature and time used in the cycle.

Embodiments of the sterilization methods described herein can achieve Sterility Assurance Levels (SAL) up to about $10^{-78}$. This is significantly higher than SAL achievable with aseptic assembly (SAL around $10^{-6}$), or the prior autoclave sterilization processes (SAL around $10^{-14}$).

As compared to prior sterilization processes, embodiments of the sterilization processes used to terminally sterilize the sealed column assembly 300 are carried out under unique conditions that facilitate sterilizing all components and surfaces of the sealed column assembly 300, including the needle-like inlet and outlet ports that are covered by the cap plugs 312. For example, embodiments of the sterilization processes described herein are carried out at generally higher temperatures, and for longer exposure times as compared to prior sterilization processes used on vented column assemblies. Moreover, embodiments of the present disclosure include introducing and mixing compressed air with saturated steam to maintain the pressure differential between the sealed column assembly and the sterilization chamber, and prevent rupture of the column assembly.

The methods of the present disclosure provide several advantages over known column assembly sterilization procedures. For example, embodiments of the methods described herein are relatively cheaper and simpler because they do not require use of a vented outlet needle cover during the sterilization process. Additionally, methods of the present disclosure are relatively cleaner because the column assembly is completely sealed during sterilization, thereby inhibiting release of radiologically contaminated steam from the column assembly. Moreover, embodiments of the methods described herein significantly reduce the risk of moisture re-entering an open or vented port of the column assembly because all ports of the elution flow path are completely sealed during the sterilization process.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method of sterilizing a column assembly within a sterilization chamber of a sterilizer, the column assembly including a column having an interior containing a retaining media and a parent radionuclide retained by the retaining media, an inlet port in fluid communication with the interior of the column, and an outlet port in fluid communication with the interior of the column, the method comprising:
   sealing at least one of the inlet port and the outlet port to form a sealed column assembly such that fluid communication with the column interior through both the inlet port and the outlet port is prevented;
   sterilizing the sealed column assembly, by exposure to a steam-air mixture including steam and compressed air, to form a terminally-sterilized column assembly; and
   controlling the rate at which compressed air is introduced into the sterilization chamber to maintain a partial pressure within the sterilization chamber substantially equal to a partial pressure within the sealed column assembly.

2. The method of claim 1, wherein sealing at least one of the inlet port and the outlet port includes covering the outlet port with an elastomeric cap, and wherein sterilizing the sealed column assembly sterilizes an exterior surface of the outlet port that is covered by the elastomeric cap.

3. The method of claim 1, wherein exposing the sealed column assembly to the steam-air mixture includes exposing the sealed column assembly to the steam-air mixture for at least 25 minutes.

4. The method of claim 1, wherein sterilizing the sealed column assembly includes:
   positioning the sealed column assembly in the sterilization chamber;
   heating the sterilization chamber to an exposure temperature of between 120° C. and 130° C.;

pressurizing the sterilization chamber to an exposure pressure of between 2000 millibars and 4000 millibars;

mixing steam and sterile compressed air within the sterilization chamber to form a steam-air mixture;

exposing the sealed column assembly to the steam-air mixture for at least 25 minutes at the exposure temperature and the exposure pressure; and controlling the rate at which compressed air is introduced into the sterilization chamber to maintain a partial pressure within the sterilization chamber substantially equal to a partial pressure within the sealed column assembly.

5. The method of claim 4, wherein the column assembly includes a fill port in fluid communication with the interior of the column, the method further including sealing the fill port to form the sealed column assembly.

6. The method of claim 1, wherein sterilizing the sealed column assembly includes subjecting the sealed column assembly to a sterilization process having an $F_0$ value of at least 40 minutes.

7. The method of claim 1, wherein controlling the rate at which compressed air is introduced into the sterilization chamber includes determining suitable set-point pressures to prevent physical deformation of the column assembly during the sterilizing step, monitoring the pressure within the sterilization chamber, wherein the rate at which compressed air is introduced is based on the set-point pressures and the monitored pressure within the sterilization chamber.

8. The method of claim 7, wherein controlling the rate at which compressed air is introduced into the sterilization chamber includes increasing the rate at which compressed air is introduced into the sterilization chamber when the monitored pressure within the sterilization chamber is more than 30 mbar below the set-point pressure, until the monitored pressure is substantially equal to the set-point pressure.

9. The method of claim 7, wherein controlling the rate at which compressed air is introduced into the sterilization chamber includes terminating the flow of compressed air into the sterilization chamber when the monitored pressure within the sterilization chamber is more than 60 mbar above the set-point pressure.

10. A method comprising:

providing a sealed radionuclide generator column assembly including a column having an interior containing a retaining media and a parent radionuclide retained by the retaining media, wherein an elution flow path of the sealed column assembly is completely sealed such that fluid flow through the column interior is prevented;

placing the sealed column assembly within a sterilization chamber of a sterilizer;

sterilizing the sealed column assembly, by exposure to a steam-air mixture including steam and compressed air, to produce a terminally-sterilized, sealed column assembly; and controlling the rate at which compressed air is introduced into the sterilization chamber to maintain a partial pressure within the sterilization chamber substantially equal to a partial pressure within the sealed column assembly.

11. The method of claim 10, wherein exposing the sealed column assembly to the steam-air mixture includes exposing the sealed column assembly to the steam-air mixture for at least 25 minutes.

12. The method of claim 10 further including heating the sterilization chamber to an exposure temperature of between 110° C. and about 130° C., and exposing the sealed column assembly to the steam-air mixture at the exposure temperature.

13. The method of claim 10, wherein providing a sealed radionuclide generator column assembly includes sealing the elution flow path of the column assembly to form the sealed column assembly.

14. The method of claim 13, wherein sealing the elution flow path includes sealing at least one of an inlet port and an outlet port of the column assembly, wherein sealing at least one of the inlet port and the outlet port prevents fluid communication with the column interior though the inlet port and the outlet port.

15. The method of claim 14, wherein sealing at least one of the inlet port and the outlet port includes covering at least one of the inlet port and the outlet port with an elastomeric cap, and wherein sterilizing the sealed column assembly sterilizes an exterior surface of at least one of the inlet port and the outlet port that is covered by the elastomeric cap.

* * * * *